United States Patent
Grotz

Patent Number: 6,017,346
Date of Patent: Jan. 25, 2000

[54] WEDGE FOR FASTENING TISSUE TO BONE

[75] Inventor: R. Thomas Grotz, San Francisco, Calif.

[73] Assignee: Ultraortho, Inc., San Francisco, Calif.

[21] Appl. No.: 09/118,391

[22] Filed: Jul. 17, 1998

Related U.S. Application Data

[60] Provisional application No. 60/053,044, Jul. 18, 1997.

[51] Int. Cl.[7] ................................................ A61B 17/56
[52] U.S. Cl. ................................ 606/72; 606/75; 606/232
[58] Field of Search ............................... 606/72, 73, 75, 606/224, 225, 232, 151

[56] References Cited

U.S. PATENT DOCUMENTS

| | | | |
|---|---|---|---|
| 5,454,814 | 10/1995 | Comte | 606/75 |
| 5,749,875 | 5/1998 | Puddu | 606/72 |

*Primary Examiner*—Michael Buiz
*Assistant Examiner*—Daphna Shai
*Attorney, Agent, or Firm*—Townsend and Townsend and Crew LLP

[57] ABSTRACT

A wedge for insertion to a rectilinear slot in bone fastens tissue for continuous refastening of separated tissue from bone. When viewed in plan toward the proximal truncated top, the wedge is sinusoidal in shape defining a series of prominences and depressions relative to the elongate slot. At the proximal end, suture fastening apertures—preferably elongate parallel to the proximal end—are placed for looping tissue fastening sutures prior to wedge insertion. A plurality of barbs—preferably placed at the prominences—together with the compression of the wedge within a rectilinear slot cause anchoring to bone upon wedge insertion to the rectilinear slot prepared within the bone. Skewering tips at the end of the wedge enable skewered tissue to be entrained with the wedge into the bone upon insertion of the bone within a previously prepared rectilinear slot. The wedge is mounted to an inserting probe and any optional sutures organized along the length of the probe. Thereafter, and utilizing the inserting probe, flesh to be inserted is conventionally "teased" onto the skewering tips and the wedge(s) inserted utilizing the probe. Fastening of the tissue entrained by the wedge within the elongate slot occurs by action of the skewers together with wedge compression of the entrained tissue at the prominences of the wedge.

17 Claims, 2 Drawing Sheets

WEDGE FOR FASTENING TISSUE TO BONE

This application claims benefit of provisional application No. 60/053044, filed Jul. 18, 1997.

FIELD OF THE INVENTION

This invention relates to the fastening of tissue to bone, such as a Bankart lesion of the shoulder. More particularly, a biocompatible wedge is disclosed, together with the method of use, and the resultant joint after surgery.

BACKGROUND OF THE INVENTION

In the fastening of tissue to bone, suture anchors have commonly been utilized. These anchors are generally known, such as the Mitek SUPERANCHOR sold by the Mitek Company of Westwood, Mass., a subsidiary of Johnson and Johnson. These anchors have as their principal object the fastening of a suture to the bone. Once the anchor is in place, the suture is either threaded around or through the tissue to be fastened to the bone. This suture must hold flesh to the bone for a sufficient period of time for healing to occur.

DISCLOSURE NOT PRIOR ART

In WO 97/07743 entitled STABILIZER FOR HUMAN JOINTS, I disclose a stabilizer device for insertion to a hole in bone that both fastens tissue to the bone and forms a suture anchor. In this device, a central body extending along a longitudinal axis forms a hollow core having laterally positioned distal and proximal faces. Bone anchors extend outwardly from the device and are barb-shaped so as to permit anchoring to bone upon expansion of the device. Centrally of the stabilizer there is provided a central plug fastened within the hollow core of the invention. Once the device is inserted within a predrilled hole in bone, the central plug expands the bone anchors, firmly anchoring the device to bone.

During insertion of the stabilizer to bone, tissue to be fastened to the bone is literally skewered at the end of the anchor. The tissue is then fastened with the stabilizer interior of the predrilled hole. Either the device can be used alone for the anchoring of tissue to bone or, alternatively, sutures anchored by the device can be used in conjunction with the skewered and fastened tissue. In one embodiment, I disclose that this material can be made from biodegradable material. Upon healing, the tissue fastens to the bone with the intended surgical repair resulting.

This device is punctate in its fastening of tissue to bone. That is to say, where tissue separates from bone, such as a Bankart's lesion in the glenoid labrum that is formed in the classical human shoulder separation, multiple stabilizers must be used in side-by-side relation to effect surgical repair. Each stabilizer forms a point of attachment of the tissue to the bone. Tissue between fasteners must be anchored by sutures. Even then, a series of fastening points are made with spatial separations therebetween. Accordingly, in the following disclosure I adapt the principles of skewered fastening in bone to the continuous fastening of tissue to bone.

SUMMARY OF THE INVENTION

A wedge for insertion into a rectilinear slot in bone fastens tissue for continuous refastening of separated tissue from bone. The wedge when directed toward the elongate rectilinear slot and viewed in side section has a distal apex of about 0.5 mm, a proximal truncated top of about 2.0 mm, and a continuous or stepped taper extending therebetween. The wedge when viewed in the plane of the rectilinear slot includes a dimension of about 8 mm from the apex to the truncated top and is about 1 cm in length. When viewed in plan toward the proximal truncated top, the wedge is sinusoidal in shape defining a series of prominences and depressions relative to the elongate slot analogous to a corrugation nail. At the proximal end, suture fastening apertures—preferably elongate parallel to the proximal end—are placed for looping tissue fastening sutures prior to wedge insertion. A plurality of barbs—preferably placed at the prominence—together with the compression of the wedge within a rectilinear slot cause anchoring to bone upon wedge insertion to the rectilinear slot prepared within the bone. Skewering tips at the end of the wedge enable skewered tissue to be entrained with the wedge into the bone upon insertion of the wedge within a previously prepared rectilinear slot in the bone.

In operation, after suitable surgical preparation and incisions preferably using arthroscopic surgical techniques, anchoring bone is exposed and a rectilinear slot is cut having a width in the order of 1.0 mm, a depth in the order of 8 mm, and an elongate length sufficient to accommodate side-by-side all wedges that are to be used. The wedge is mounted to an inserting probe and any optional sutures organized along the length of the probe. Thereafter, and utilizing the inserting probe, flesh to be inserted is conventionally "teased" onto the skewering tips and the wedge(s) inserted utilizing the probe. Fastening of the tissue entrained by the wedge within the elongate slot occurs by action of the skewers together with wedge compression of the entrained tissue at the prominences of the wedge. At the same time, flesh to be reattached to the bone can optimally vascularize at the defined depressions between the wedge and rectilinear slot in the bone. There results an improved fastener for flesh to bone, an improved method utilizing the fastener for securing flesh to bone, and finally a novel reconstructed bone/flesh interface for healing to the bone.

DESCRIPTION OF THE PREFERRED EMBODIMENTS

Figure 1A:
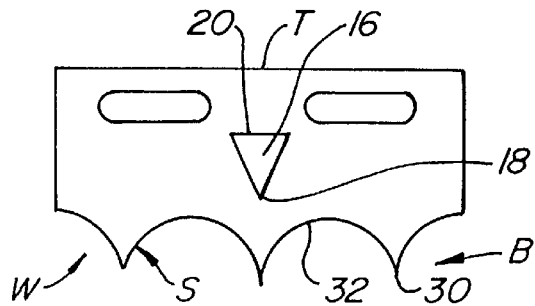
FIG. 1A is a front elevation illustrating the wedge with protruding barbs, bottom skewers. and elongate suture holding apertures.
Figure 1B:
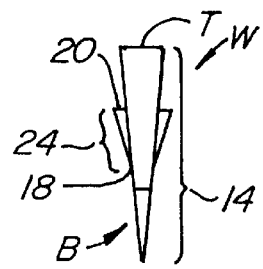
FIG. 1B is a side elevation illustrating the wedge shaped cross-section with the barbs in profile for holding the wedge to bone.
Figure 1C:
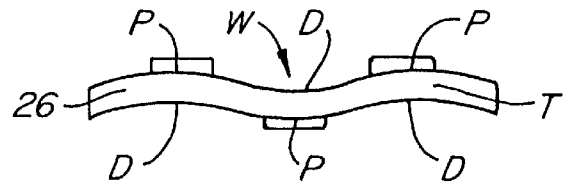
FIG. 1C is a top plan view of the wedge illustrating the slight sinusoidal configuration defining alternating prominences and depressions with barbs at the prominences for keying the wedge to bone.
Figure 2A:
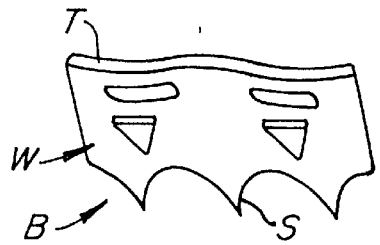
FIGS. 2A and 2B are perspective views of the wedge.
Figure 2B:
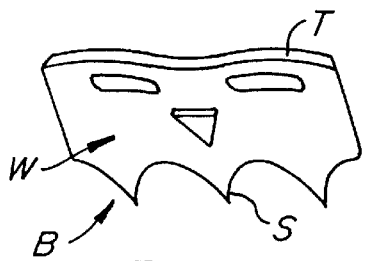

Referring to FIGS. 1A–1C, wedge W is shown. Wedge W includes proximal top T, distal bottom B, with wedge W defining continuous taper 14 therebetween (see FIG. 1B). In a dimension capable of being utilized on the average adult human, wedge W is 1 cm side to side (see FIG. 1A), 8 mm top to bottom (see again FIG. 1A), 0.5 mm at distal bottom B, and 2 mm at proximal top T.

It is preferable that wedge W, when entered into a previously prepared slot in bone, wedge itself into engagement with the bone. Three factors assist such wedging.

First, wedge W defines continuous taper 14 from distal bottom B to proximal top T. Providing that the prepared slot in bone has a dimension less than wedge W at proximal top T, wedging of wedge W into bone will occur.

Second, and with respect to FIG. 1C, wedge W at proximal top T is given a curved profile so as to define prominences P and depressions D. At prominences P, barbs R are located and typically have a triangular shape with barb apex 18 adjacent distal bottom B and barb truncated prominence 20 towards proximal top T. As can be seen in FIG. 1B, section 22 of barbs R increases with taper 24 from the proximal to the distal portion of wedge W. Thus it will be understood that as wedge W is driven to wedge into bone, barbs R will anchor to such bone with truncated prominence 20 keying into substantial bone mass.

Finally, prominences P and depressions D here impart to wedge W at proximal top T sinusoidal profile 26. Upon wedging of wedge W to bone, respective prominences P compress rendering depressions D with a lesser depth. Consequently, compression of sinusoidal profile 26 results in further holding of wedge W to bone.

Finally, wedge W has skewers S adjacent and defined in distal bottom B. Skewers S are here shown defined within distal bottom B by round cuts 32. These leave skewer points 30 for impaling tissue with rounded flats 32 therebetween to contain and compress gathered tissue. It will be understood that skewer points 30 thus impale but do not cut tissue and enable impaled tissue to be entrained with the wedge into a previously prepared bone slot.

It will be understood that depressions D serve a serendipitous function. Specifically, the purpose of wedge W is to enable impaled tissue to reattach to bone. Depressions D define a spatial interval between a previously prepared bone slot and wedge W. In this area, vascularization readily occurs with reattachment through bone/tissue growth rapidly occurring.

Finally, suture apertures 33 are preferably provided. These suture apertures 33 are preferably oblong parallel to proximal top T. Sutures are conventionally threaded through such apertures. It is important to note that unlike the case of the conventional suture anchor, sutures here are optional— and not required. Indeed it is a preferred use of the disclosed apparatus that sutures can be omitted entirely.

Wedge W can be made of biocompatible or physiologically inert materials. Such materials include titanium and its alloys, stainless steel, and cobalt-based alloys or plastics. Bioabsorbable materials are preferred. These include aliphatic polyesters of alpha-hydroxy acid derivatives as described in Rokkanen, P. V. (1991) "Absorbable Materials in Orthopedic Surgery," Annals of Med. 23:109–115.

Figure 3:
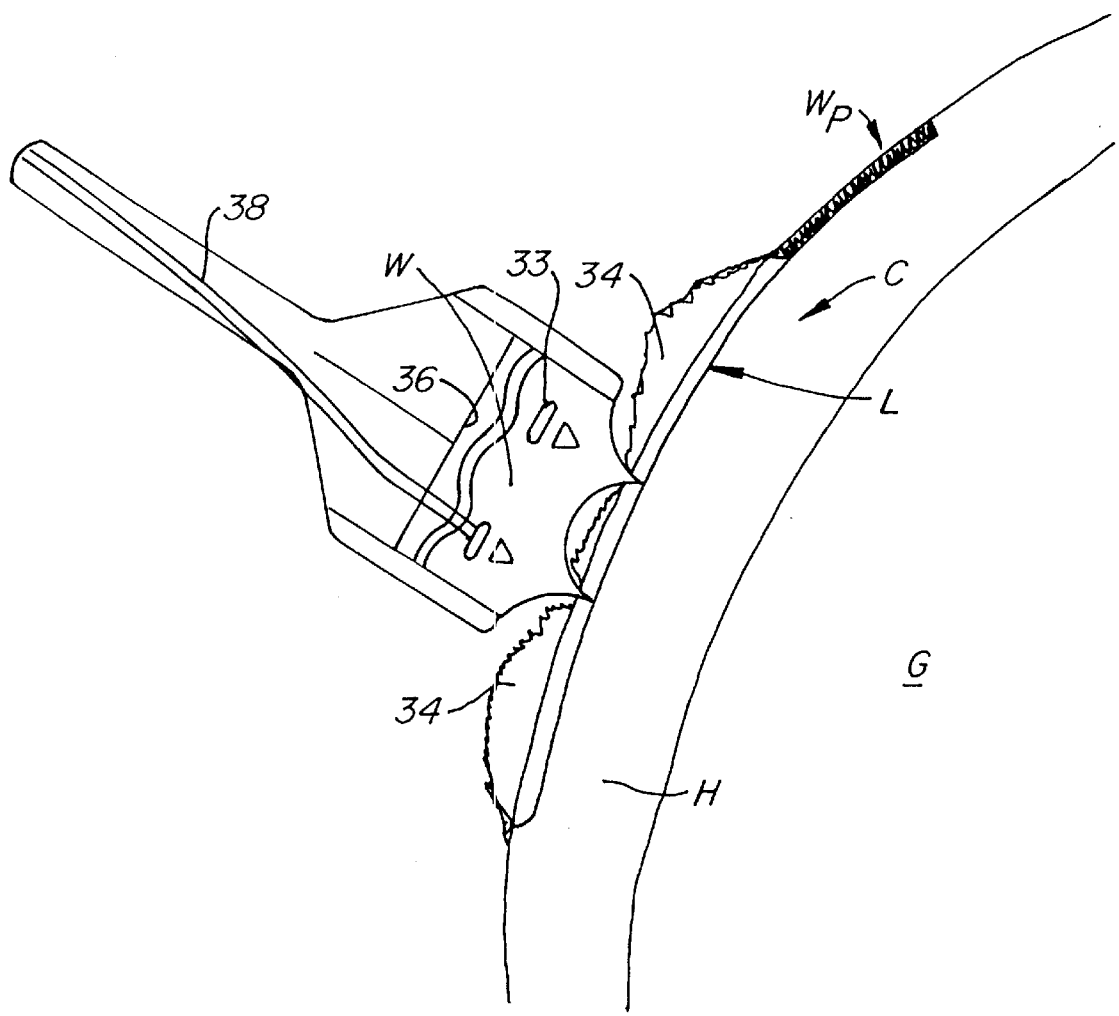
FIG. 3 is a perspective view of one wedge fully inserted within the insertion slot, skewering and wedging tissue into place with an optional suture protruding from the slot with an inserter and a second wedge overlying the same previously prepared insertion slot having teased and skewered tissue impaled as the second wedge is about to be inserted into the slot.
Figure 4:
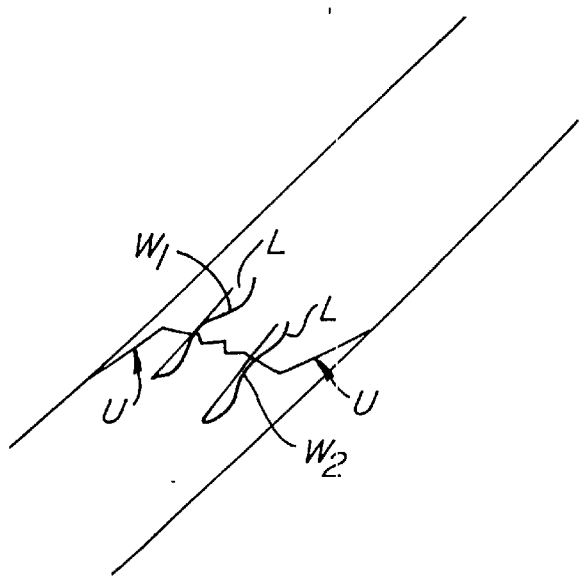
FIG. 4 is a plan view of two wedges holding separated and broken bone into apposition for healing.

Reference is now made to FIGS. 3 and 4. The reader will understand that preferred surgical techniques here utilized are through arthroscopic surgical techniques. In the description that follows, it will first be assumed that such arthroscopic techniques have "exposed" bone and flesh to be fastened. Thereafter, and for the operating orthopedic doctor, a verbal description will be given of a shoulder repair utilizing the apparatus and method of this invention. For simplicity, elaborate illustration of the surgical technique will not be provided.

Referring to FIG. 3 and providing an oversimplified explanation, a perspective schematic view of a shoulder operation underway is illustrated. Glenoid cup G is shown with fibrocartilage F having tissue tears 34 forming a so-called Bankart lesion. Slot L has been cut in glenoid rim C to a depth of about 8 mm. Wedge $W_P$ has been previously placed, entraining tissue into slot L cut in glenoid rim C. Inserter I specifically adapted for placement of wedge W into slot L is illustrated and can be easily understood.

Inserter I has a dimension for introduction by trocar. It includes folded U-shaped ends E trapping wedge W therebetween. Proximal top T with its sinusoidal profile 26 abuts wedge driving end 36. As shown, suture 38 may optionally be both "organized" to inserter I as well as assist in maintaining wedge W to inserter I. Such holding of suture 38 can occur either at notches within inserter I or by wrappings about inserter I such as an elastic rubber ring (neither shown).

Inserter I is utilized to "tease" tissue to be skewered onto skewers S at distal bottom B of wedge W. Thereafter, wedge W is inserted to slot L entraining tissue to be fastened to the bone. This causes tissue tears 34 to be refastened to glenoid rim C where conventional healing may occur.

It will be understood with respect to FIG. 4 that this wedge W can be used for holding separated or broken bones in apposition. Two wedges $W_1$ and $W_2$ are each illustrated placed across fracture U in the single bone illustrated. In this case, slot L is cut substantially normal to the parting of the bone with the respective wedges causing apposition until healing.

Having set forth a general description, use of the invention herein within a shoulder repair of a shoulder having a Bankart's lesion is now set forth for a specific example of use of a wedge made in accordance with the present invention.

Before incisions are made, wedge W should be prepared on inserter I so that it is properly fixed in an effort to avoid detachment. If sutures are desired, they should be placed by the surgeon selecting the suture of choice and the number of sutures intended for use. The inserter and the wedge should be placed on the operating table proximate to the wound area and kept sterile. Next, the incisions are made.

In the case of the repair of a shoulder with a Bankart's lesion, surgery can be limited to two incisions. One is anterior and one lateral in the shoulder. This surgery can be done through two wounds, one anterior one-half inch or 1 cm wound and one lateral 0.5 cm or quarter-inch wound. In order to do it with only two wounds, one needs to use the current 3M Arthroscopic Trocar and cannula sold by the 3M Company of Minneapolis, Minn., which has three portals of external joint attachment. These three portals are used for inflow, outflow and for the 3M pump pressure gauge. By using that external portal system, one of the usual arthroscopic wounds can be eliminated and the arthroscopic lateral wound is placed 1 cm posterior to the greater tuberosity of the humerus, 1 cm beneath the inferior acromion lateral cortex in the palpable "dent or divot" just behind the lateral aspect of the humeral head. That wound is made horizontally or perpendicular to the axis of the body a quarter inch in size and with the assistant surgeon distracting distally the arm.

A blunt trocar is entered posterior to the insertion of the supraspinatus tendon, i.e., the rotator cuff on the greater tuberosity, and it is directed toward the anterior rim of the glenoid, thus entering the shoulder with the 3M trocar and its blunt trocar directional device. The anterior wound is made a half inch in length also perpendicular to the axis of the body or horizontal, and it is located medial to the biceps tendon slightly lateral to the anterior gleno-humeral joint line 1 cm inferior to the inferior acromion.

The second wound is the anterior one-half inch wound, the larger of the two wounds, and it is made just lateral to the gleno-humeral joint 1 or 2 cm beneath the inferior cortex of the acromion.

The lateral smaller wound is for arthroscopic visualization for fluid ingress and egress if a 3M portal system is available. If the 3M portal system is not available, then a third wound must be made posteriorly along the gleno-humeral joint a centimeter or two beneath the inferior acromion a quarter inch in length horizontal and could be used for a 3M pump or other pump application to allow for egress and pressure measurement.

The anterior wound in any case is the working portal. It has the largest wound, one-half inch in length, and is entered with a blunt device including the cannula and center rounded trocar from the anterior shoulder skin toward the posterior back of the shoulder aiming for the gleno-humeral joint line. The cannula most suited for this procedure is the Smith Nephew 1 cm diameter newly produced device.

Once in the gleno-humeral joint, the Smith Nephew blunt trocar is removed and synovitis or debris is removed as the joint is irrigated through the cannula. Careful inspection of the joint is then obtained by using a probe to determine the amount of separation of the glenoid labrum from the glenoid fossa per se.

If a significant lesion is determined by the primary surgeon to be a Bankart lesion worthy of repair, then the edge along the anterior glenoid rim is prepared by using the arthroscopic debrider, such as an ARTHROWAND device for tissue ablation, or and/or a burr to expose a linear superficial layer of exposed bone. The purpose of this is to denude the cortex and create an adjacent superficial vascularity that will bring a small amount of bleeding bone to the foreground, thus allowing repair tissue perfusion with oxygen and nutrients once the tissue repair is complete.

The lesion is studied as regards its length and the type of repair necessary is determined. If the lesion is 1 cm or greater, the wedge application would be appropriate. Instead of drilling a hole, as one would do conventionally, an oscillating saw or similarly functioning device made for this purpose is passed through the cannula from the anterior to posterior, through the anterior shoulder wound and pre-placed cannula, and it is directed aligned longitudinally with the avulsion site of origin over the prepared bone and a slot is made. The slot is made to cover the length of injury tissue and is approximately 1 mm wide and 8 mm deep.

The saw is removed and any additional debris removed and inspection is preformed again.

The wedge is then introduced and lined up parallel with the segment of avulsed tissue to be reconnected. It enters that tissue and approaches it with the skewers S necessarily angulated in such a manner so as to be able to skewer the tissue from anterior and direct it posteriorly toward and ultimately into the base of the slot.

The wedge is next impacted on its proximal end (towards the surgeon) until the wider surface of the wedge is flush with the surface of the prepared bone. At this point, the inserter is released from the wedge and the optional sutures are used if desired to engage any additional necessary tissue repair or reefing of a patchulous joint. This is done with the routine suture passing equipment and according to the technique chosen by the primary surgeon.

Thereafter, withdrawal of cannulae and closure of all wounds occurs with the surgery essentially being complete.

It will be understood that I have illustrated my invention with a particular emphasis on the repair of Bankart lesions in the shoulder. Clearly, other repairs for fastening of tissue to bone utilizing this device may be made. By way of example, knee repair can likewise be made.

Considering repair of other parts of the body, it will be understood that the preferred dimension set forth herein can change. By way of example, for repair of certain parts of the leg and knee, dimensions of wedges W shown herein can be as much as 3 cm of width and 1 cm of depth, or for the rotator cuff attaching tendon to bone, a wedge 2 cm wide and 1 cm in depth may be used.

I have used the term "tissue" in describing the fastening of flesh or biocompatible synthetic material to bone. The fastening of certain biocompatible materials to bone can work as well.

Further, I contemplate the use of the wedge herein for fastening tissue to tissue. In this case, the illustrated slotting of bone can be dispensed with. A wedge with entrained tissue can force its own opening to the tissue into which fastening or refastening is to occur, such as in repairing longitudinal fibrocartilage tears.

What is claimed is:

1. A wedge for insertion to an elongate rectilinear slot in bone for fastening tissue to bone comprising:

a wedge having a distal apex, a proximal top of and a taper extending between the distal apex and the proximal top;

the wedge when viewed in plan toward the proximal top defining a series of prominences and depressions;

a plurality of barbs for acting upon compression of the wedge within a rectilinear slot to cause anchoring to bone upon wedge insertion to the rectilinear slot prepared within the bone; and, skewering tips at the distal apex of the wedge to enable skewered tissue to be entrained with the wedge into the bone upon insertion of the wedge within a previously prepared rectilinear slot.

2. A wedge for insertion to an elongate rectilinear slot in bone according to claim 1 and further including:

the wedge is fabricated from biocompatable material chosen from the group consisting of biodegradeable material, physiologically inert materials and bioabsorbable materials.

3. A wedge for insertion to an elongate rectilinear slot in bone according to claim 1 and further including:

a dimension of about 0.5 mm at the distal apex; and a dimension of about 2.0 mm at the proximal top.

4. A wedge for insertion to an elongate rectilinear slot in bone according to claim 1 and further including:

the wedge when viewed in plan toward the proximal top defining a slightly sinusoidal curve.

5. A wedge for insertion to an elongate rectilinear slot in bone according to claim 1 and further including:

the wedge when viewed in a plane coincident to the rectilinear slot includes a dimension of about 8 mm from the distal apex to the proximal top.

6. A wedge for insertion to an elongate rectilinear slot in bone according to claim 1 and further including:

the wedge when viewed in a plane coincident to the rectilinear slot including a dimension of about 1 cm along the proximal top of the wedge.

7. A wedge for insertion to an elongate rectilinear slot in bone according to claim 1 and further including:

the wedge adjacent the proximal top defining suture fastening apertures.

8. A wedge for insertion to an elongate rectilinear slot in bone according to claim 7 and further including:

the suture fastening apertures are elongate parallel to the proximal top.

9. A wedge for insertion to an elongate rectilinear slot in bone according to claim 7 and further including:

at least one suture placed through the suture fastening aperture for tissue fastening.

10. A wedge for insertion to an elongate rectilinear slot in bone according to claim 1 and further including:

the plurality of barbs for acting upon compression of the wedge within the rectilinear slot are placed at the prominences.

11. A wedge for insertion to an elongate rectilinear slot in bone according to claim 1 and further including:

the plurality of barbs have a triangular section with an apex of the triangular section disposed distally and a base of the triangular section disposed proximally.

12. A wedge for insertion to an elongate rectilinear slot across separated bone for fastening the separated bone in apposition comprising:

a wedge having a distal apex, a proximal top of and a taper extending between the distal apex and the proximal top;

the wedge when viewed in plan toward the proximal top defining a series of prominences and depressions; and, a plurality of barbs for acting upon compression of the wedge within a rectilinear slot to cause anchoring to bone upon wedge insertion to the rectilinear slot prepared within the bone.

13. A wedge for insertion to an elongate rectilinear slot across separated bone for fastening the separated bone in apposition according to claim 12 comprising:

skewering tips at the distal apex of the wedge to enable skewered tissue to be entrained with the wedge into the bone upon insertion of the wedge within a previously prepared rectilinear slot.

14. The combination of a wedge inserter and wedge for wedge insertion to an elongate rectilinear slot in bone for fastening tissue to bone comprising:

a wedge having a distal apex, a proximal top of and a taper extending between the distal apex and the proximal top;

the wedge when viewed in plan toward the proximal top defining a series of prominences and depressions;

a plurality of barbs for acting upon compression of the wedge within a rectilinear slot to cause anchoring to bone upon wedge insertion to the rectilinear slot prepared within the bone; and, skewering tips at the distal apex of the wedge to enable skewered tissue to be entrained with the wedge into the bone upon insertion of the wedge within a previously prepared rectilinear slot;

a wedge inserter having a distal end and a proximal end;

means on the distal end of the wedge inserter for receiving the distal top of the wedge and disposing the proximal apex for insertion to the rectilinear slot.

15. The combination of a wedge inserter and wedge for wedge insertion to an elongate rectilinear slot in bone for fastening tissue to bone according to claim 14 further comprising:

the wedge adjacent the proximal top defines at least one suture fastening aperture;

at least one suture is threaded through the suture fastening aperture; and, one end of the at least one suture is fastened to the wedge inserter.

16. A method for fastening tissue to bone comprising:

providing a wedge having a distal apex, a proximal top and a taper extending between the distal apex and the proximal top;

the wedge when viewed in plan toward the proximal top defining a series of prominences and depressions;

a plurality of barbs for acting upon compression of the wedge within a rectilinear slot to cause anchoring to bone upon wedge insertion to the rectilinear slot prepared within the bone;

skewering tips at the distal apex of the wedge to enable skewered tissue to be entrained with the wedge into the bone upon insertion of the wedge within a previously prepared rectilinear slot;

cutting an elongate rectilinear slot in bone for receiving the wedge under compression;

skewering tissue to be fastened to the bone on the skewering tips of the wedge; and, inserting the wedge to the rectilinear slot in the bone to entrain tissue with the wedge into the bone.

17. A combination including tissue fastened to bone comprising:

a wedge having a distal apex, a proximal top and a taper extending between the distal apex and the proximal top;

the wedge when viewed in plan toward the proximal top defining a series of prominences and depressions;

a plurality of barbs for acting upon compression of the wedge within a rectilinear slot to cause anchoring to bone upon wedge insertion to the rectilinear slot prepared within the bone;

skewering tips at the distal apex of the wedge to enable skewered tissue to be entrained with the wedge into the bone upon insertion of the wedge within a previously prepared rectilinear slot;

an elongate rectilinear slot in bone for receiving the wedge under compression;

skewered tissue fastened to the bone on the skewering tips of the wedge; and, the wedge inserted to the rectilinear slot in the bone to entrain tissue with the wedge into the bone.

* * * * *